United States Patent [19]

Greco et al.

[11] Patent Number: 4,670,573

[45] Date of Patent: Jun. 2, 1987

[54] ACTIVATED PREPARATION OF METAL ALKOXIDES

[75] Inventors: Carl C. Greco, Garnerville, N.Y.; Kelly B. Triplett, Stamford, Conn.

[73] Assignee: Stauffer Chemical Company, Westport, Conn.

[21] Appl. No.: 682,641

[22] Filed: Dec. 17, 1984

[51] Int. Cl.$^4$ .............................................. C07F 5/06
[52] U.S. Cl. ........................................ 556/182; 556/1; 556/122; 568/851
[58] Field of Search .............. 568/851; 260/448 AD, 260/429 R; 556/1, 122, 182; 534/10, 11, 15

[56] References Cited

U.S. PATENT DOCUMENTS

| | | |
|---|---|---|
| 2,666,076 | 1/1954 | Rex et al. . |
| 2,796,326 | 6/1957 | Kimberlin et al. .......... 260/448 AD |
| 2,845,447 | 7/1958 | Carlson . |
| 2,927,937 | 3/1960 | Gaines . |
| 3,083,218 | 3/1963 | Hammerberg ............. 260/448 AD |
| 3,094,546 | 6/1963 | Towers ........................... 568/851 X |
| 3,239,568 | 3/1966 | De Pree et al. ............... 568/851 X |
| 3,507,896 | 4/1970 | Jones et al. .................. 260/448 AD |
| 3,523,129 | 8/1970 | Holbert et al. ............. 260/448 AD |
| 3,523,130 | 8/1970 | Jones et al. .................. 260/448 AD |
| 3,641,077 | 2/1972 | Rochow .................................... 556/1 |
| 3,717,666 | 2/1973 | Kobetz et al. . |
| 3,890,166 | 6/1975 | Kondis . |
| 3,963,482 | 6/1976 | Kondis . |
| 4,042,636 | 8/1977 | Lenz et al. .......................... 568/851 |
| 4,288,604 | 9/1981 | Magee et al. . |

FOREIGN PATENT DOCUMENTS

| | | | |
|---|---|---|---|
| 517360 | 10/1955 | Canada ................................ 568/851 |
| 2612642 | 9/1977 | Fed. Rep. of Germany ...... 568/851 |
| 727923 | 4/1955 | United Kingdom ................ 568/851 |

OTHER PUBLICATIONS

Kirk-Othmer's *Encyclopedia of Chemical Technology*, Third Edition, vol. 2, (1978), pp. 1–17.
*Metal Alkoxides*, by D. C. Bradley et al., (1978), pp. 10–13.
"The Preparation and Some Properties of Yttrium, Disprosium, and Ytterbium Alkoxides", by K. S. Mazdiyasni et al., *Inorganic Chemistry*, vol. 5, No. 3 (1966), pp. 342–346.
*Alcoa Aluminum Powder in the Chemicals and Plastics Industries*, (Revised Jun. 1982), Section PAP 918 (FA2-D-3), Alcoa Tech. Bull.

*Primary Examiner*—Helen M. S. Sneed

[57] ABSTRACT

There are disclosed improved methods for preparing metal alkoxides from metals and alcohols. The methods involve dry-grinding the metal in an inert atmosphere prior to the addition of the alcohol. When an activator is used, it is usually ballmilled with the metal. Higher yields are obtained, particularly when the metal and alcohol are not very reactive absent an activator. Typical metals are those from Groups 2A, 2B, 3A, and 3B, particularly aluminum, magnesium, and yttrium. Typical alcohols are those which contain up to 16 carbon atoms, particularly those containing 4 or more carbon atoms.

16 Claims, No Drawings

ACTIVATED PREPARATION OF METAL ALKOXIDES

BACKGROUND (i) Field of the Invention

This invention relates generally to activated preparation of metal alkoxides from metals and alcohols. More particularly, it concerns preparing alkoxides from certain metals and certain alcohols which are not very reactive absent an activator. Typical metals are those from groups 2A, 2B, 3A and 3B. Typical alcohols are those which contain up to 16 carbon atoms. The activators include both catalysts and noncatalysts. Even more particularly, it relates to ball milling the activator and the metal prior to the addition of the alcohol.

(ii) Description of the Prior Art

The use of activators in preparing metal alkoxides from metals and alcohols has been known for decades. Accordingly, summaries of the prior art are available in handbooks. For example, Kirk-Othmer's "Chemical Encyclopedia", Third Edition, summarizes such preparation in the following manner (for a monovalent metal).

"*From Metals and Alcohol*: Alkali, alkaline earth metals, and aluminum react with alcohols to give metal alkoxides (2-3,61):

The speed of the reaction depends both on the metal and on the alcohol, increasing with increasing electropositivity and decreasing with length and branching of the chain. Thus sodium reacts strongly with ethanol, but slowly with tertiary butanol. The reaction with alkali metals is sometimes carried out in ether, benzene, or xylene. Some processes use the metal amalgam or hydride instead of the free metal. Alkaline earth metals and aluminum are almost always covered with an oxide film. Slight etching with iodine or mercuric chloride breaks the film and facilitates the reaction".

Aforementioned Kirk-Othmer also discusses their preparation by alcoholysis and transesterification and points out the following: "Metal alkoxides of higher, unsaturated, or branched alcohols are difficult to prepare directly and are usually made from lower metal alkoxides by means of alcoholysis:

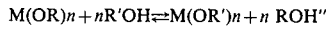

An even more comprehensive recent survey is found in "Metal Alkoxides" by D. C. Bradley, R. C. Mehrotra and D. P. Gaur, published by the Academic Press in 1978. "Reactions of Metals with Alcohols" is discussed at pages 10–13 and it is stated that a catalyst "appears to be essential" for "the less electropositive elements such as magnesium, beryllium and aluminum"; and perhaps for yttrium and scandium. It further states that the role of the catalyst in such reactions is not fully understood, but it might involve merely cleaning the metal surface or perhaps the formation of intermediate derivatives which could react more readily with alcohols.

Significantly, neither of the foregoing surveys discloses or suggests that there could be any advantage from grinding an activator and a metal prior to addition of the alcohol.

A computer search of Chemical Abstracts from 1967 to present, concerning the preparation of metal alkoxides, did not turn up any reference which, from its abstract, clearly related to the grinding of a metal. Also, it turned up only one reference which, from it's abstract, clearly related to the use of a catalyst in preparing a metal alkoxide from metal and alcohol. This reference is U.S. Pat. No. 3,717,666 (Kobetz et al.), discussed below.

Aforementioned Kobetz discloses that the reaction of aluminum and alcohol is improved by catalysis with an alkoxy alcohol. The reference states that an important advantage of the Kobetz invention is that it does not require "activation by alloying or mixing with mercury or its compounds, halogens, titanium, silicon, zirconium, sodium, etc. or the need for physical manipulations such as cutting, grinding, powdering or abrading to exceedingly fine particle sizes". The same reference refers to U.S. Pat. Nos. 2,125,961; 2,229,528; 2,579,251; 2,636,865; and 2,666,076.

Aforementioned U.S. Pat. No. 2,636,865 (Kimberlin) relates to preparing aluminum alkoxides by a process wherein there is not even pre-mixing of the catalytic material and the aluminum prior to the addition of the alcohol (for example, see the description in Col. 4, from line 50 to line 68).

Aforementioned U.S. Pat. No. 2,666,076 (Rex et al.) relates to a process for making aluminum alkoxide from aluminum and amyl alcohol or the like. Rex's invention relates to a continuous process wherein large pieces of aluminum are treated with an activating solution (such as a 1% solution of mercuric chloride in amyl alcohol) thereby removing an oxide film from the metal surface; separating the activated aluminum from at least most of the activating solution; and reacting the activated aluminum with an alcohol such as amyl alcohol at elevated temperature. Rex points out that the prior art (as of 1952) "operated largely on the belief that the activation of the aluminum was essentially a catalytic effect, and consequently activating solutions have heretofore generally been added to the main reaction mixture, thereby leading to undesirable contamination". Rex includes a number of negative teachings relative to the invention claimed hereinafter.

U.S. Pat. No. 2,845,447 (Carlson) was cited against aforementioned Kobetz. Carlson appears to relate to an autocatalytic process which "can proceed without added catalyst due to the aluminum in the upper part of the bed being conditioned by the presence of the liquid in the reaction zone in the lower part of the bed" (see claim 1 and col. 6, lines 52–75).

The preparation of yttrium alkoxides is discussed in the "The Preparation and Some Properties of Yttrium, Disprosium, and Ytterbium Alkoxides" by K. S. Mazdiyasni, C. T. Lynch, and J. S. Smith in "Inorganic Chemistry", Vol. 5, No. 3, March, 1966 at pages 342–346. Working examples for yttrium are provided at pages 343–344, for both aliphatic and aromatic compounds; as well as synthesis of heavier alkoxides by substitution of other R groups for the isopropoxy group in an alcoholysis reaction. Yields ranged from 47% to 85%. Interestingly the reference teaches that the reaction can be carried out "in excess alcohol but not in excess mercuric chloride" because of the side reaction in which the alcohol reacts to form an alkene and to produce an alkene oxide as the finished product (see discussion at pages 344–345). The foregoing would appear to be a strong negative teaching against any process involving dry ball milling of mercuric chloride with fine particles of heavily indented and serrated metal, and perhaps forming local high concentrations of mercuric chloride in the crevices.

A second computer search of Chemical Abstracts from 1967 to present was made. This search concerned ball milling of metal as the broadest category. This turned up two references of interest, which are discussed below.

U.S. Pat. No. 3,890,166 (Kondis, hereinafter Kondis 1) relates to the milling of particulate aluminum in the presence of a material capable of sorbing onto the surface of the aluminum sufficiently to stabilize it and at the same time be readily displacable, thereby producing a reactive or pyrophoric aluminum (see Abstract). The whole of the patent is hereby incorporated by reference. Significantly, all of Kondis' actual working examples appear to relate to wet grinding, rather than dry grinding (for example see Table 1, "milling media"; Table 2, "milling conditions"; and Table 3, "carrier liquid".

U.S. Pat. No. 3,963,482 (Kondis hereinafter Kondis 2) is related to aforementioned Kondis 1. It teaches that "(i)mproved aluminum particulate suitable for powder metallurgy application is produced by wet-milling particulate aluminum in an inert atmosphere in the presence of a predetermined amount of oxygen to thereby comminute the aluminum into finer particles while oxidizing the new surfaces of such particles and then, after the supply of oxygen is exhausted, welding together such particles by further milling to provide a larger aluminum particle having aluminum oxide dispersed therein (see Abstract). The whole of this patent is also hereby incorporated by reference.

There is also extensive trade literature concerning aluminum powders that are commercially available. "Alcoa Aluminum Powder in the Chemicals and Plastics Industries" is of particular interest since the aluminum used in the examples of the invention hereinafter was obtained from Alcoa and aforementioned Kondis assigned his patents to Alcoa. FIGS. 7 and 8 of the reference relate to the production of linear primary alcohols from activated aluminum powder, wherein aluminum alkoxides are intermediates.

Applicants' copending application Ser. No. 656,380, filed Oct. 1, 1984, includes a conventional method of preparing di-isobutyl, n-butyl aluminum alkoxide (see it's Comparative Example C-1). In that example, no dry-grinding was performed.

In sum, even with the benefit of hindsight, none of the aforementioned references disclose or suggest the invention claimed hereinafter which is restricted to dry grinding.

SUMMARY OF THE INVENTION

In contrast to the prestep of the aforementioned prior art, there has been found an improved process for preparing a metal alkoxide by reacting a metal with an alcohol in the presence of an activator, wherein the improvement comprises the prestep of dry-grinding the metal with the activator. There has also been found an improved process for preparing the alkoxide by reacting a metal with an alcohol wherein the improvement comprises the prestep of dry-grinding the metal in an inert atmosphere and maintaining the inert atmosphere at least until addition of the alcohol.

DESCRIPTION OF THE PREFERRED EMBODIMENTS

All embodiments of the invention involve "dry-grinding" of at least the metal. The term "dry-grinding", as used herein, includes grinding wherein a liquid is present in an amount of up to 15% by weight based on the weight of the metal. When the metal is ground by itself, it is essential that the grinding be performed in an inert atmosphere. When the metal is ground with an activator, it is usually preferred that it be ground in an inert atmosphere.

Preferred metals for use in this invention include those from Groups 2A, 2B, 3A, and 3B of the Periodic Table. The invention is particularly suitable for use with aluminum, magnesium, yttrium, barium, and thallium. Examples of the invention with aluminum, magnesium, and yttrium are provided below. It is preferred that the metal be in the form of fine particles rather than chunks or shavings. It is also preferred that the metal be of high purity and that the particles contain less than 1% by weight of metal oxide. Particle sizes are relatively non-critical, particularly because some breakdown of particles occurs during the grinding operation. It is generally preferred, however, that the particle sizes be less than 50 mesh (U.S. Standard). In the examples concerning aluminum below, the particle diameter was 25–28 microns, with about half of the product capable of passing a 325 mesh screen (U.S. Standard).

When an activator is milled with the metal, choice of activator will depend in part upon the particular metal alkoxide to be prepared. In general, the activator includes catalysts (including auto-catalysts); and non-catalysts, such as those which remove oxide films and those which form an intermediate product with the metal, which intermediate product reacts more readily with the alcohol. It is preferred that the activator be present in an amount of up to 10 weight percent based on the weight of the metal. It is more preferred that the activator be present in an amount of up to 1 weight percent. The activator may be present in the form of a solid or a liquid. Mixtures of solid and liquid activators may be used beneficially (for example, see Example 13A below).

The preferred alcohols used in the invention are those which contain up to 16 carbon atoms. More preferably they contain from 3 to 10 carbon atoms and most preferably 4 to 8 carbon atoms. The alcohols may be saturated or unsaturated, branched or unbranched. Typical alcohols include the following: ethyl alcohol; isopropyl alcohol; n- propyl alcohol; n-butyl alcohol; isobutyl alcohol; sec-butyl alcohol; n-amyl alcohol; isoamyl alcohol; n-hexyl alcohol; 2-ethylhexyl alcohol; and mixtures thereof.

The preferred embodiments of the prestep of the invention are particularly those that lead to higher yields of alkoxide (and not merely higher reaction rates) and/or a catalyst-free reaction resulting in absence of need to purify the final product by removal of the catalyst. Accordingly, a quick appreciation of some of the preferred embodiments of the invention will be obtained by reviewing Tables 1, 2, and 3 below which tables summarize essential data concerning yield and processing conditions of most of the working examples given below. In this context, it should be noted that all examples having the suffix "A" or "B" are examples of the invention. All examples having the suffix "C" are comparative examples, but are not necessarily examples from the prior art. In particular, all the "A" examples involved milling both metal and activator. All the "B" examples involved milling the metal without any activator being present. All the "C" examples involved processes in which there was no pre-milling of the metal prior to reaction with the alcohol. It will be noted that all the Comparative Examples in all the tables had lower yields than corresponding working Examples of the invention. It will also be noted that the yield can be significantly affected by the type of metal, the type of alcohol, and the type of activator.

The invention, of course, is not limited to the actual working examples shown herein, but rather includes the conditions defined in the claims hereinafter. Examples of the invention and comparative examples now follow.

EXAMPLE 1A

Commercially available samples of aluminum powder, n-amyl alcohol, and mercuric chloride were obtained. The aluminum powder was Alcoa's high purity atomized powder No. 7124. According to the manufacturer's product data sheet (dated 8-77), aluminum powder 7124 is high purity powder recommended for use as ball mill feed to produce special aluminum pigments. According to the data sheet properties of the aluminum powder included the following. The average particle diameter was 25-28 microns, with about half of the product capable of passing a 325 mesh screen (U.S. Standard). It had a surface area of 0.10-0.20 square meters per gram, and an apparent density of 1.2 grams per cc. The particles were at least 99.97% aluminum (excluding 0.5% $Al_2O_3$ which exists on the surface of the particles). The mercuric chloride was in granular form having particle sizes similar to those of table salt.

Aluminum powder (25 grams), mercuric chloride (0.3 grams), stainless steel balls (⅜ inch, 875 grams) were placed in a ball mill jar (1 liter capacity), and blanketed with nitrogen. The mill jar was closed and then rotated at room temperature for six hours at about 100 rpm. The mill was opened in an inert atmosphere and the contents sieved through a 20 mesh screen which separated the balls from the activated aluminum.

A portion of the activated aluminum (12 grams) was reacted with n-amyl alcohol (200 grams) at 120°-140° C. The alcohol was placed in a 500 ml. flask, equipped with a stirrer, solid addition funnel and condenser. The alcohol was heated to 120° C. with 1 gram of the aluminum powder. At this temperature, the remainder of the aluminum was added portion wise over 30 minutes. During this period there was vigorous evolution of hydrogen. Hydrogen evolution appeared to stop after about 12 hours but the reaction was continued at this temperature for a total period of 24 hours in order to insure completion of the reaction. The reaction product was then filtered using a Celite TM filtering aid to remove unreacted aluminum metal. The filtrate was then stripped to constant weight by removing the excess alcohol in a conventional manner. The desired aluminum tris-n-amyl oxide remained in 90% yield, based on the weight of the aluminum powder.

COMPARATIVE EXAMPLE 1C

Example 1A was repeated except that no milling operation was performed. Also, the mercuric chloride was added to the alcohol prior to the addition of the aluminum powder. The yield was only 70% in contrast to Example 1A.

A number of further experiments were then performed using the same aluminum powder and alcohol, but different activator systems. The results are summarized in Table 1 below.

TABLE 1

| | Percent Yields from Aluminum and n-Amyl Alcohol | | |
|---|---|---|---|
| | Milled Ingredients | | |
| (Ex. Nos.)/ Activator | Metal and Activator | Metal | None |
| (1A and 1C)/ mercuric chloride | 90 | | 70 |
| (2A, 2B and 2C)/ sodium butyl carbitolate | 92 | 94 | 85 and 88 |
| (3A)/ butyl carbitol | 87 | | |
| (4B and 4C)/ none | — | 83 | 72 |
| (5C)/ iodine | | | 69 |

EXAMPLES 2A, 2B AND COMPARATIVE EXAMPLE 2C

These examples illustrate the yields obtained when sodium butyl carbitolate is used as a catalyst.

In Example 2A, Example 1A was repeated in all respects except that 0.08 grams of sodium butyl carbitolate (instead of mercuric chloride) was milled with 11.0 grams of aluminum powder. The yield of alkoxide was 92%.

In Example 2B, Example 2A was repeated in all respects except that the catalyst was not milled with the aluminum. Instead, the catalyst was added to the milled aluminum and alcohol in the reactor. The yield was 94%.

In Comparative Example 2C, Comparative Example 1C was repeated except that sodium butyl carbitolate (0.17 grams) was used as the catalyst. The yield was 85%. In an essential repeat of this Example (using 12 grams of aluminum and 0.84 grams of catalyst) the yield was found to be 88%.

EXAMPLE 3A

Example 1A was repeated in all respects except that two grams of butyl carbitol was milled with 11.5 grams of aluminum powder. The butyl carbitol reacted with the aluminum to form a catalytic amount of aluminum butyl carbitolate. The solid composition was then reacted with n-amyl alcohol according to Example 1A. The yield of product was 87%.

EXAMPLE 4B AND COMPARATIVE EXAMPLE 4C

These Examples illustrate the yields obtained when no catalyst was used.

In Example 4B, Example 2B was repeated except that no catalyst was used. The yield was 83%.

In Comparative Example 4C, Comparative Example 2C was repeated in all respects except that no catalyst was used. The yield was 72%.

COMPARATIVE EXAMPLE 5C

Comparative Example 1C was repeated in all respects except that iodine (0.1 gram) was used in place of mercuric chloride. The yield of alkoxide was 69%.

EXAMPLE 6A TO COMPARATIVE EXAMPLE 9C

These Examples illustrate the yields obtained when the metal is magnesium and the alcohol is ethanol. The magnesium used was Valiment TM. No trade literature was received thereon, but the product was understood to be 50-200 mesh prepared by milling in an inert atmosphere. In all these Examples the magnesium was blanketed with toluene prior to addition of the alcohol (approximately 20 grams of magnesium for each 150-200 milliliters of toluene). The results of all these Examples are summarized in Table 2 below.

In Example 6A, Example 1A was essentially repeated except for the different metal and different alcohol. The yield was found to be 90%.

In Example 7B, Example 2B was essentially repeated except for the different metal and different alcohol. The yield was found to be 95%.

In Example 8A, Example 3A was essentially repeated except for the different metal and different alcohol. The yield was found to be 75%.

In Example 9B, Example 4B was essentially repeated except for the different metal and different alcohol. Yields of 93% and 95% were obtained in duplicate trials.

In Comparative Example 9C, Comparative Example 4C was essentially repeated except for the different metal and the different alcohol. The yields obtained in triplicate trials were 90%, 87%, and 90%.

TABLE 2

Percent Yields from Magnesium and Ethanol

| (Ex. Nos.) Activator | Ingredients Milled | | |
|---|---|---|---|
| | Metal and Activator | Metal | None |
| (6A)/ mercuric chloride | 90 | | |
| (73)/ sodium butyl carbitolate | | 95 | |
| (8A)/ butyl carbitol | 75 | | |
| (9B and (C)/ none | — | 93 and 95 | 90, 87 and 90 |

It should be noted, however, that magnesium (which is more electropositive than aluminum) and ethanol are highly reactive. Accordingly, the foregoing results do not really bring out the advantages of the invention when higher alcohols are reacted with magnesium.

EXAMPLE 10A TO COMPARATIVE EXAMPLE 11C

In all these Examples, yttrium was used as the metal and isopropyl alcohol as the alcohol. The yttrium came in the form of shavings or chunks from Alfa Inorganics. The yttrium was reacted with a large excess of isopropyl alcohol (about 25-50 grams of yttrium in one liter of alcohol).

In Example 10A, Example 1A was essentially repeated except for the different metal and different alcohol. Yields of 46 and 46.5% were obtained in duplicate runs.

In Example 10B, Example 10A was essentially repeated except that the yttrium was milled without the mercuric chloride being present. The yield of alkoxide was 44%.

In Comparative Example 10C, Comparative Example 1C was essentially repeated except for the different metal and different alcohol. A yield of only 10% was obtained.

In Comparative Example 11C, Comparative Example 10C was repeated except that no mercuric chloride was used. The yield was 0%.

Table 3 below summarizes the foregoing data relevant to yttrium.

TABLE 3

Percent Yields from Yttrium and Isopropyl Alcohol

| (Ex. Nos.)/ Activator | Milled Ingredients | | |
|---|---|---|---|
| | Metals and Activator | Metal | None |
| (10A, 10B and 10C) mercuric chloride | 46 and 46.5 | 44 | 10 |
| (11C)/ None | — | | 0 |

COMPARATIVE EXAMPLE 12C

Comparative Example 11C was essentially repeated except that the yttrium was in a different mechanical form. In particular, the yttrium was in pre-ground form and had a particle size roughly corresponding to the yttrium in Example 10B after being ground. The yield was 0%.

EXAMPLE 12A

Example 1A was repeated in all respects except that sec-butyl alcohol was used as the reactant instead of n-amyl alcohol. The yield of aluminum tris-sec-butoxide was 95%.

EXAMPLE 13A

Example 12A was repeated except that in addition a small amount of butyl carbitol (0.1 gram) was added prior to ball milling. It was found that the product had reduced tendency to agglomerate and to stick to the inner walls of the milling jar (as compared to Example 1A). The yield of alkoxide was 95%.

What we claim is:

1. An improved process for preparing a metal alkoxide by reacting a metal, M, having a particle size less than 50 mesh and wherein M is selected from aluminum, barium, magnesium and yttrium with an alcohol, ROH, comtaining up to 16 carbon atoms, in the presence of an activator, A, selected fron the group consisting of butyl carbitol, sodium butyl carbitol, mercuric chloride, and iodine; wherein the improvement comprises, the prestep of drygrinding M with A.

2. The process of claim 1 wherein A is a catalyst for the reaction of M with ROH.

3. The process of claim 1 wherein the prestep comprises ball-milling M with A.

4. The process of claim 3 wherein A is a liquid and which comprises ball-milling at least until there is a significant amount of agglomeration of M and A throughout the whole of the mixture of M and A.

5. The process of claim 4 which comprises ball-milling for a period of at least 8 hours in an inert atmosphere.

6. The process of claim 3 wherein the mixture being ball-milled further comprises an alcohol containing up to 16 carbon atoms in an amount of up to 10 weight percent based upon the weight of the weight of M.

7. The process of claim 6 wherein the alcohol in the mixture contains up to 5 carbon atoms.

8. The process of claim 6 wherein the alcohol in the mixture has the same structural formula as the alcohol ROH that is used in the subsequent process step.

9. The process of claim 1 wherein M is in the form of fine particles having a surface oxide layer in an amount of up to 1% by weight based on the weight of metal M.

10. The process of claim 1 wherein the activator is present in an amount of up to 10% of weight based upon the weight of the metal.

11. The process of claim 2 wherein A is capable of reacting with M to form a reaction product, and the reaction product is an autocatalyst for the reaction of M with ROH.

12. The process of claim 2 wherein the catalyst is present in an amount of up to 10 weight percent based on the weight of metal.

13. The process of claim 1 wherein A is a noncatalyst for the reaction of M with ROH.

14. The process of claim 13 wherein A is capable of reacting with oxides of M.

15. The process of claim 13 wherein A is capable of reacting with M.

16. The process of claim 1 which comprises alcohols selected from the group consisting of ethyl alcohol; isopropyl alcohol; n-propyl alcohol; n-butyl alcohol; isobutyl alcohol; sec-butyl alcohol; n-amyl alcohol; isoamyl alcohol; n-hexyl alcohol; 2-ethylhexyl alcohol; and mixtures thereof.

* * * * *

UNITED STATES PATENT AND TRADEMARK OFFICE
CERTIFICATE OF CORRECTION

PATENT NO. : 4,670,573
DATED : June 2, 1987
INVENTOR(S) : Carl C. Greco et al.

It is certified that error appears in the above-identified patent and that said Letters Patent are hereby corrected as shown below:

Col. 3, line 30, "therein (see Abstract)" should read --therein" (see Abstract)--;

Col. 8, line 7, a slash mark (/) should appear after "(10A, 10B and 10C)";

Col. 8, line 40, "comtaining" should read --containing--; and

Col. 8, line 44, "drygrinding" should read --dry grinding--.

Signed and Sealed this

Twenty-second Day of September, 1987

Attest:

DONALD J. QUIGG

Attesting Officer     Commissioner of Patents and Trademarks